United States Patent [19]
McLucas

[11] Patent Number: 5,348,023
[45] Date of Patent: Sep. 20, 1994

[54] CURETTING INSTRUMENT AND METHOD

[76] Inventor: Bruce McLucas, 100 UCLA Medical Plz., Suite 310, Los Angeles, Calif. 90024-6970

[21] Appl. No.: 869,739

[22] Filed: Apr. 16, 1992

[51] Int. Cl.⁵ ............................................. A61B 17/00
[52] U.S. Cl. .................................. 128/757; 606/160; 606/170; 30/325
[58] Field of Search ................. 128/757; 606/160, 161, 606/167, 162, 170; 30/132, 324, 325, 346, 150

[56] References Cited

U.S. PATENT DOCUMENTS

| | | | |
|---|---|---|---|
| 1,784,575 | 12/1930 | Carlson | 30/325 |
| 2,425,917 | 8/1947 | Brignola | 606/161 |
| 2,770,877 | 11/1956 | Bird | 30/324 |
| 4,984,367 | 1/1991 | Albanese | 30/324 |
| 5,026,386 | 6/1991 | Michelson | 606/170 |

FOREIGN PATENT DOCUMENTS

| | | | |
|---|---|---|---|
| 1468514 | 3/1989 | U.S.S.R. | 606/160 |
| 2204496 | 11/1988 | United Kingdom | 128/757 |

*Primary Examiner*—Stephen C. Pellegrino
*Assistant Examiner*—Gary Jackson
*Attorney, Agent, or Firm*—Limbach & Limbach

[57] ABSTRACT

An improved curette is disclosed having a spoon-shaped scoop attached to an elongated tapered handle. Substantially the entire periphery of the scoop is sharpened, allowing the curette to be used in a lateral or rotating motion to remove and collect tissue samples. The new curette also has a sharpened interior edge on its forward end allowing curetting when drawing the instrument backward. Small drainage holes through the bottom of the scoop allow the curette to efficiently capture more tissue.

3 Claims, 1 Drawing Sheet

CURETTING INSTRUMENT AND METHOD

BACKGROUND OF THE INVENTION

1. Field of the Invention

This invention relates to surgical instruments used for scraping or cutting tissue for removal and collection. More particularly, it is concerned with endocervical curettes for removing tissue specimens from the cervix. Such specimens are needed for biopsies when cervical cancer is suspected.

2. Discussion of the Prior Art

Numerous curette designs have been the subject of patents since at least the turn of the century. These various designs usually include a handle for positioning the surgical instrument inside a cavity of the body, a means for removing tissue, such as a sharp blade or scraper, and a means for collecting the tissue specimen. U.S. Pat. Nos. 839,641, 4,043,322 and 4,221,222 are examples of such devices. Traditionally, tissue is removed by moving these curettes in a back and forth manner. The removed tissue is then typically trapped in the "basket" of the curette (e.g. two bands of steel across the bottom of the curette.)

SUMMARY OF THE INVENTION

The curette of the present invention is easier to use than those of the prior art in that tissue is easier to remove and collect with the new instrument.

The present invention has a spoon-shaped end for removing and collecting tissue. Because the spoon-shaped end has an oval shape and almost its entire periphery is sharpened, tissue may be sharply curetted in several ways, such as by using the sides of the curette in a lateral, rotating motion, or by using the end of the curette in a traditional back and forth motion.

The spoon shape of the end of the instrument also has the advantage of efficiently collecting tissue specimens. Drainage holes are provided through the bottom of the curette to allow fluids to drain from the curette without washing away the tissue specimens.

The present invention permits more tissue to be retained in the curette. This provides more tissue for pathologic evaluation and less loss of tissue that must be curetted from the patient.

The foregoing advantages of the invention will be apparent from the following descriptions and the accompanying drawings.

DETAILED DESCRIPTION OF THE PREFERRED EMBODIMENTS

Figure 3:
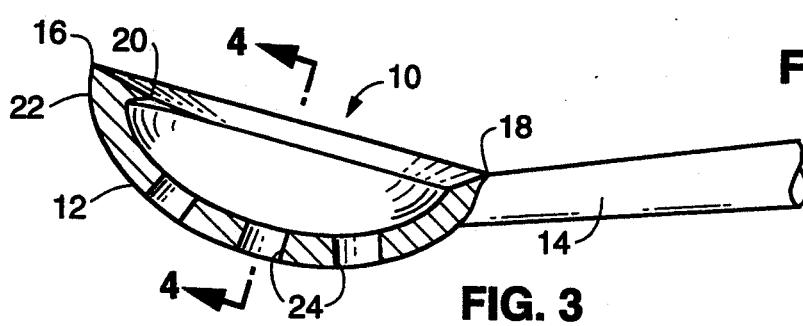
FIG. 3 is a side view in partial cross section taken along line 3—3 of FIG. 2.

The curette 10 of the present invention comprises a spoon-shaped scoop 12 integrally formed on the narrow end of a tapered handle 14. As best seen in FIG. 3, the scoop 12 forms an obtuse angle with the handle 14 of about 10 degrees.

The entire upper, outer peripheral edge 16 of the scoop 12 is sharpened, except for a small connecting region 18 where the scoop 12 joins the handle 14. In addition to the sharpened peripheral edge 16, an upper, overhanging, interior edge 20 is sharpened and located in the forward portion 22 of the scoop 12. Both the sharpened peripheral edge 16 of the scoop 12 and the sharpened interior edge 20 can be easily re-sharpened, if needed after use, in a single operation.

Drainage holes 24 are provided through the bottom of the scoop 12 allowing blood and fluids to exit the scoop 12, but retaining the collected tissue sample or samples in the scoop 12. In the preferred embodiment, there are three drainage holes 24, each 0.04–0.05 inches in diameter.

Figure 5:
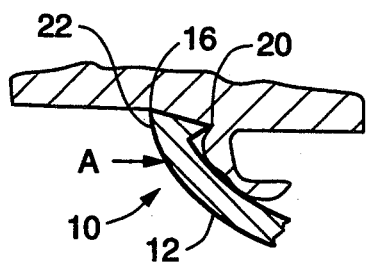
FIG. 5 is a partial side view in cross section representing tissue removal by a longitudinal translation of the curette.
Figure 6:
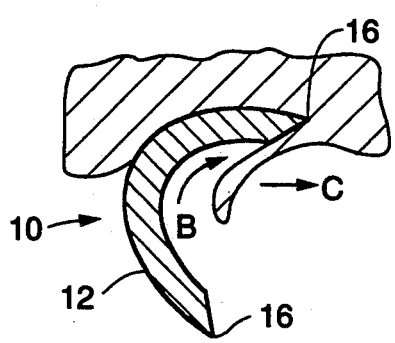
FIG. 6 is a partial end view in cross section representing tissue removal by a lateral translation and/or rotation of the curette about its longitudinal axis.

FIGS. 5 and 6 illustrate the two basic techniques used with the new curette 10 to remove and collect tissue. As shown in FIG. 5, the curette 10, once inserted into the body, can be pulled backwards in the direction of arrow A. This causes the sharpened interior edge 20 to engage the tissue and remove a sample that is then collected in the scoop 12. Alternatively, the curette 10 can be rotated in the direction of arrows BB, as shown in FIG. 6, to sharply curette the tissue. To increase the length of the tissue sample, the curette 10 is moved in the direction of arrows CC as it is rotated in the direction of arrow B. In all three cases above, the curetted tissue specimen tends to be guided down into the scoop 12 for collection.

Figure 1:
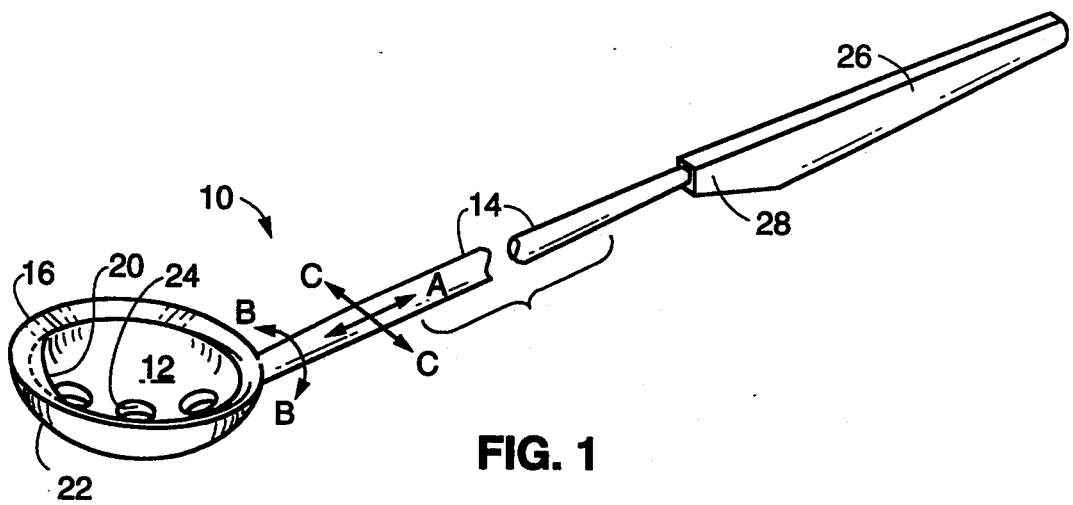
FIG. 1 is a pictorial view of the scraping and collecting end of the curette in accordance with the present invention.
Figure 2:
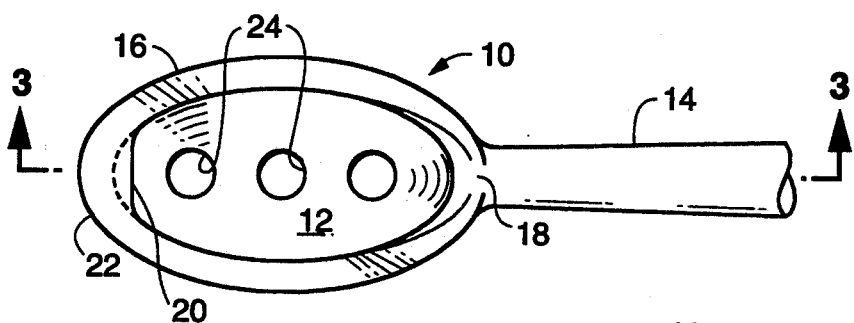
FIG. 2 is a plan view of the portion of the curette illustrated in FIG. 1.
Figure 4:
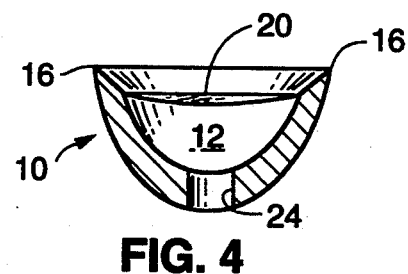
FIG. 4 is an end view in cross section taken along line 4—4 of FIG. 3.

The upper grip portion 26 of the handle 14 is substantially wider and thicker than the lower half, providing a more comfortable and controllable gripping surface with which the user holds the instrument. As shown in FIGS. 2 and 3, the upper grip portion 26 is plate-like and has its widest dimension in the vertical direction (perpendicular to the peripheral edge 16.) The grip portion 26 is tapered so that it increases in width towards the middle of the handle 14. A chamfer 28 is provided on the forward end of the grip portion (as shown in FIG. 3) to accommodate the forefinger of the user. Because the instrument is symmetrical, either the left or the right hand many be used. This arrangement allows the user to accurately control the rotation of the instrument by pinching the grip portion between the thumb on the top edge and the forefinger on the bottom chamfer 28. The remaining fingers curl around the taper of the grip portion. This handle design provides comfortable, ergonomic control of the instrument while being simple and inexpensive to manufacture.

In the preferred embodiment of the present invention, the length, width, and total depth of the scoop 12 are roughly 0.38, 0.24, and 0.12 inches, respectively. The overall length of the instrument is approximately 9 inches.

The curette 10 is constructed from surgical grade stainless steel and the finished instrument is one unitary piece. The scoop 12 is hardened to allow the sharpened edges to remain sharp longer.

It is to be understood that the present invention is not limited to the sole embodiment described above and illustrated herein, but encompasses any and all variations falling within the scope of the appended claims.

I claim:

1. A method of obtaining tissue from inside a living body, the method comprising the steps of:
   inserting a curette inside the body, said curette comprising a handle, an oval spoon-shaped member connected to said handle for collecting the tissue, a sharp edge formed on substantially the entire upper perimeter of said spoon-shaped member, and an overhanging sharp edge formed on an inside edge of said upper perimeter on a forward end of said collection means for removing the tissue from the body;
   moving said inserted curette to cause one or more cutting edges on said curette to cut tissue and place said tissue in the spoon-shaped member;
   removing tissue from the inside of the body with said curette;
   collecting the removed tissue in said spoon-shaped member of said curette; and
   withdrawing said curette and said collected tissue from the body.

2. A curette comprising:
   an elongated handle having a longitudinal axis;
   removal means for cutting or scraping tissue;
   collection means for retaining the tissue, said collection means being attached to an end of said handle, said collection means being concave and spoon shaped and having an upper periphery, said upper periphery being oval-shaped and having an outer edge lying substantially in a plane;
   said removal means including a sharp edge formed on and around said outer edge of said upper periphery of said collection means;
   said sharp edge extends substantially entirely around said outer edge of the upper periphery; and
   said removal means further includes an overhanging sharp edge formed on an inside edge of said upper periphery on a forward end of said collection means opposite said handle.

3. A curette comprising:
   an elongated handle having a longitudinal axis;
   removal means for cutting or scraping tissue;
   collection means for retaining the tissue, said collection means being attached to an end of said handle, said collection means being concave and spoon shaped and having an upper periphery, said upper periphery being oval-shaped and having an outer edge lying substantially in a plane; and
   said removal means including a sharp edge formed on and extending substantially entirely around said outer edge of said upper periphery of said collection means and an overhanging sharp edge formed on an inside edge of said upper periphery on a forward end of said collection means opposite said handle.

* * * * *